(12) United States Patent
John et al.

(10) Patent No.: US 8,961,879 B2
(45) Date of Patent: Feb. 24, 2015

(54) CURABLE COMPOSITIONS CONTAINING COLOR INDICATORS FOR INDICATING THE CURING PROGRESS

(75) Inventors: Guenther John, Schwarzenbek (DE); Stefanie Ehmke (nee Behrens Brammertz), Hamburg (DE)

(73) Assignee: Mankiewicz Gebr. & Co. GmbH & Co. KG, Hamburg (DE)

( * ) Notice: Subject to any disclaimer, the term of this patent is extended or adjusted under 35 U.S.C. 154(b) by 75 days.

(21) Appl. No.: 12/736,471

(22) PCT Filed: Mar. 19, 2009

(86) PCT No.: PCT/DE2009/000360
§ 371 (c)(1),
(2), (4) Date: Oct. 12, 2010

(87) PCT Pub. No.: WO2009/127182
PCT Pub. Date: Oct. 22, 2009

(65) Prior Publication Data
US 2011/0024690 A1    Feb. 3, 2011

(30) Foreign Application Priority Data

Apr. 15, 2008 (DE) ............ 10 2008 019 017

(51) Int. Cl.
*G01N 21/75* (2006.01)
*G01N 21/78* (2006.01)
*C08G 18/36* (2006.01)
*C08G 18/66* (2006.01)

(52) U.S. Cl.
CPC ............. *G01N 21/78* (2013.01); *C08G 18/36* (2013.01); *C08G 18/6662* (2013.01); *C08G 2190/00* (2013.01)
USPC ............ 422/82.05; 436/5; 436/166; 521/134; 521/138; 528/52; 528/53

(58) Field of Classification Search
CPC ................................................. G01N 21/78
USPC ............ 521/134, 138; 528/52, 53; 422/82.05; 436/5, 166
See application file for complete search history.

(56) References Cited

U.S. PATENT DOCUMENTS

| | | | |
|---|---|---|---|
| 5,071,887 A * | 12/1991 | Nakagawa et al. | 521/137 |
| 5,228,782 A | 7/1993 | Imer | |
| 5,302,627 A | 4/1994 | Field et al. | |
| 5,854,358 A * | 12/1998 | Heinemann et al. | 525/404 |
| 6,060,544 A * | 5/2000 | Keen | 524/190 |
| 6,066,436 A | 5/2000 | Kumpfmiller et al. | |
| 6,423,472 B1 * | 7/2002 | Kumpfmiller et al. | 430/284.1 |
| 2003/0175488 A1* | 9/2003 | Asthana et al. | 428/212 |
| 2008/0261052 A1 | 10/2008 | Xia et al. | |

FOREIGN PATENT DOCUMENTS

| | | |
|---|---|---|
| DE | 101 15 004 | 10/2002 |
| EP | 0 492 380 | 7/1992 |
| EP | 0 492 830 | 7/1992 |
| FR | 2 237 922 | 2/1975 |
| FR | 2237922 * | 2/1975 |
| WO | WO 98/10003 | 3/1998 |
| WO | WO 03/046061 | 6/2003 |

OTHER PUBLICATIONS

Colour Index International, Society of Dyers and Colourists.
Solvent Blue 104 Basic Information, Chemical Book.
Solvent Red 195 Basic Information, Chemical Book.
Disperse Yellow 64 Basic Information, Chemical Book.
Solvent Green 28 Basic Information, Chemical Book.
Disperse Violet 26 Basic Information, Chemical Book. (also known as Solvent Violet 59).
Solvent Red 179 Basic Information, Chemical Book.
Solvent Violet 13 Basic Information, Chemical Book.
C.I. 564100 Basic Information, Chemical Book. (Solvent Orange 60).
Solvent Green 3 Basic Information, Chemical Book.

* cited by examiner

*Primary Examiner* — Sally Merkling
(74) *Attorney, Agent, or Firm* — Collard & Roe, P.C.

(57) ABSTRACT

The invention relates to curable compositions which are prepared from polyol components containing one or more polyols and isocyanate components containing one or more isocyanates, which compositions contain at least one indicator having at least one quinonoid group, which indicator signifies the degree of curing by a change of color. The invention also relates to a method for indicating the progress of curing in such curable compositions.

19 Claims, No Drawings

CURABLE COMPOSITIONS CONTAINING COLOR INDICATORS FOR INDICATING THE CURING PROGRESS

CROSS REFERENCE TO RELATED APPLICATIONS

This application is the National Stage of PCT/DE2009/000360 filed on Mar. 19, 2009, which claims priority under 35 U.S.C. §119 of German Application No. 10 2008 019 017.9 filed on Apr. 15, 2008, the disclosure of which is incorporated by reference. The international application under PCT article 21(2) was not published in English.

The present invention relates to means and a method for indicating the curing progress in curable compositions, particularly in dual component polyurethane systems, and the use of dyes containing quinoniod groups as color indicators in compositions prepared from isocyanates.

Polymers that are obtained by polyaddition of dihydric or polyhydric alcohols and isocyanates are referred to as polyurethanes (PUR). Conventional polyurethanes are produced from polyester diols and polyether diols and diisocyanates such as toluene diisocyanate (TDI), 4,4'-methylene diphenyl isocyanate (MDI) or hexamethylene diisocyanate (HMDI). The use of diols and isocyanates in equimolar ratios leads to linear polyurethanes. Branched and cross-linked products are produced when higher-functionality educts are used as supplements to the polyurethane synthesis or also when there is an excess of isocyanate, in which case isocyanate groups react with urethane groups or urea groups. Certain amines and organic tin and zirconium compounds are used as catalysts for the polyaddition. Usually, polyurethanes are produced as prepolymers having terminal isocyanate groups, which, when used, for example, as sealing compositions, and are cured under the action of moisture from the atmosphere, leading to chain extension and, possibly, to crosslinking. Such prepolymers can also be chain-extended with diamines to produce polyurethanes containing urea groups.

Polyurethane foams are formed when the polyaddition is carried out in the presence of water or carboxylic acids. These react with the isocyanates with the elimination of carbon dioxide, which has an expanding and foam-forming action. Polyurethane-based resins are referred to as polyurethane resins. They are produced, for example, by the reaction of monoglycerides and diglycerides with diisocyanates such as toluene diisocyanate (TDI). Polyurethane resins also include polyurethane prepolymers terminated by free or blocked isocyanate group, which are cured under the action of moisture.

Depending on the choice of starting materials selected and their stoichiometric ratio, polyurethanes can be produced with very different mechanical properties. They can be used, for example, as constituents of adhesives and coatings primarily in the form of polyurethane resins, as polyether-urethane or polyester-urethane rubber, as thermosetting casting resins, and as foamed plastics.

The term "polyurethane system" used below is understood to mean all polymers that contain chain-extending or crosslinking urethane groups derived from the reaction of isocyanates with polyols.

Usually, dual component polyurethane systems are used as coating, insulating, and sealing compositions. In these systems, one component contains the polyols and the other component, also referred to as the curing agent, contains the isocyanates. Prior to application, the two components are mixed and the mixture is then cured. The prerequisite for a uniform curing process is the thorough mixing of the two components. Furthermore, particularly polyurethane systems that are to be processed further must be fully cured prior to further processing. With conventionally used dual component polyurethane systems, it is difficult to determine when the mixture of the components is homogeneous and when the resulting composition is fully cured.

It is known to use a dye or pigment in each of the two components of a polyurethane system, which dyes or pigments initially differ from each other but on mixing form a new color. This, however, indicates exclusively the homogeneity of the mixture.

The use of pH indicators is known for monitoring the progress of curing. Thus DE 101 15 004 A1 describes a moisture-curing polyurethane system that contains, prior to moisture curing, an excess of isocyanate groups and is produced from compositions having at least two isocyanate groups, compositions having at least two hydrogen atoms capable of reacting with isocyanate groups, and an amine compound. This polyurethane system contains a pH indicator that indicates the degree of curing of the system, i.e. the increase in pH due to the increase in free amine groups during the curing process, by a change of color.

However, the use of a pH indicator is not suitable for polyurethane systems showing no significant change in pH during the curing process.

It is therefore an object of the present invention to provide means and a method for improving the indication of the curing progress in curable compositions, more particularly in compositions that are prepared from dual component polyurethane systems.

This object is achieved by means of a curable composition and a method for optically indicating the degree of curing as defined in the independent claims. Preferred embodiments are the subject matter of the subordinate claims and are described below.

It has been found, surprisingly, that the progress of the curing process involved in the production and curing of compositions made from dual component polyurethane systems is indicated by a change of color of substances containing at least one quinoniod group. The dual component polyurethane system of the invention includes at least one component containing one or more polyols and at least one further component containing one or more isocyanates.

Substances containing one or more quinoniod groups, more particularly dyes or pigments, are used as color indicators. For the purposes of the present invention, the term "quinoniod groups" is understood to mean carbon rings, more particularly 6-membered ring systems having conjugated double bonds but no aromaticity. Quinoniod groups and systems are usually formed by the dearomatization of benzoid systems. Particular preference is given to anthraquinone dyes and anthraquinone pigments such as Solvent Blue 104, Solvent Green 3, Solvent Violet 59, Solvent Green 28, Solvent Violet 13, Solvent Red 195, Solvent Orange 60, Solvent Red 179, Disperse Violet 26 and Disperse Yellow 64

In a preferred embodiment, at least one anthraquinone dye or anthraquinone pigment is added to the composition, more preferably to the polyol component, in a concentration of from 0.1 to 500 ppm, based on the weight of the polyol component. The amount added is dependent on the dye or pigment used and the content of compounds present in the composition or the polyol component, respectively. At concentrations of less than 0.1 ppm, the color intensity is generally not sufficient for identification of a change of color. On the other hand, concentrations exceeding 500 ppm are no longer necessary for enhancing the identification of a change of color.

Furthermore, the polyol component, as well as the isocyanate component, can contain further substances familiar to the person skilled in the art and conventionally used for imparting specific properties to the compositions of the invention. For example, fillers, catalysts, plasticizers, and other additives such as flame retardants, molecular sieves, and stabilizers can be added to the components.

Moreover, it is preferred according, to the invention, to add further dyes and/or pigments to the isocyanate component in order to indicate the homogeneity of the mixture of polyol and isocyanate components. Examples of suitable dyes and pigments are Solvent Blue 104 and Violet 13.

The homogeneity of the mixture of the invention becomes evident when no further colored streaks are visible and a uniform color has been achieved. The change of color indicating the progress of the curing process sets in as the polyol and isocyanate components are mixed together during the mixing process, and the new color intensifies as curing of the composition progresses. The degree of color change depends on the concentration of the color indicator and the overall formulation of the composition.

The polyol component of the composition of the invention includes one or more polyols. Preferred polyols are polypropylene glycols (PPG), polyethylene glycols (PEG), castor oil, polyols based on castor oil, and other polyols based on oils of vegetable and animal origin, polyols based on polyesters, polycaprolactones, polytetrahydrofurans, and hydroxy-functional polyacrylates, and mixtures thereof. Monoglycerides of fatty oils are particularly preferred fur use in the method of the invention.

The isocyanate component of the composition of the invention includes one or more isocyanates. Preferred isocyanates are diisocyanatomethylbenzene (toluene diisocyanate (TDI)) and isomers and mixtures thereof, diisocyanatodiphenylmethane (diphenylmethane-diisocyanate (MDI)), and isomers and homologs and mixtures thereof, 1,6-diisocyanatohexane (hexamethylene diisocyanate (HDI)), 3,5,5-trimethyl-1-isocyanato-3-isocyanatomethylcyclohexane (isophorone diisocyanate (IPDI)), 4,4'-diisocyanatodicyclohexylmethane ($H_{12}$MDI) and isomers and mixtures thereof, 1,3-bis(isocyanato-methyl)benzene (m-xylylene diisocyanate (XDI)), 1,6-diisocyanato-2,2,4(2,2,4)trimethylhexane (TMDI) and isomers and mixtures thereof, and mixtures of two or more of the aforementioned diisocyanates. Additional preferred isocyanates are adducts of diisocyanates and polyhydric alcohols such as the adduct of diisocyanato-methylbenzene (TDI) with trimethylolpropane (TMP) available under the trade name DESMODUR L marketed by Bayer AG, oligomers of diisocyanates such as isocyanurates, biurets, allophanates and uretdiones and prepolymers obtainable by the reaction of diisocyanates with hydroxy-functional polymers or oligomers. Particular preference is given to diisocyanatodiphenylmethane (MDI) and isomers and homologs and mixtures thereof, adducts of diisocyanates and polyhydric alcohols such as the adduct of diisocyanatomethylbenzene (TDI) with trimethylolpropane (TMP), oligomers of diisocyanates such as isocyanurates, biurets, allophanates and uretdiones and prepolymers obtainable by the reaction of diisocyanates with hydroxy-functional polymers or oligomers, and greater preference is given to diisocyanato-diphenylmethane (MDI) and isomers and homologs and mixtures thereof.

The compositions of the invention can be used, for example, as coating, insulating, and sealing compositions.

According to the invention, dyes and pigments indicating a change of color in the presence of isocyanate groups are suitable for use as color indicators for indicating the degree of curing of compositions produced from isocyanates. Preferred dyes and pigments have at least one quinoniod group. According to the invention, most preference is given to the use of anthraquinone dyes and anthraquinone pigments such as Solvent Blue 104, Solvent Green 3, Solvent Violet 59, Solvent Green 28, Solvent Violet 13, Solvent Red 195, Solvent Orange 60, Solvent Red 179, Disperse Violet 26 and Disperse Yellow 64.

In a further aspect, the object of the present invention is achieved by means of a method for visually indicating the progress of the curing process of a composition, particularly a dual component polyurethane system, producible using at least one polyol component and at least one isocyanate component, in which method (a) one or more color indicators indicating a change of color in the presence of isocyanate groups are added to the polyol component, and additional dyes and/or pigments are optionally added to the isocyanate component, (b) a composition is formed by mixing the polyol and isocyanate components until the mixture has a uniform coloration, and (c) the composition is cured, the completion of the curing process being indicated by a change of color.

In a preferred embodiment of the method of the invention, dyes and pigments having at least one quinoniod group are used as color indicators. According to the invention, use is very preferably made of anthraquinone dyes and anthraquinone pigments such as Solvent Blue 104, Solvent Green 3, Solvent Violet 59, Solvent Green 28, Solvent Violet 13, Solvent Red 195, Solvent Orange 60, Solvent Red 179, Disperse Violet 26 and Disperse Yellow 64.

Preferably, the method of the invention is carried out using a polyol component containing one or more polyols selected from the group consisting of polypropylene glycols (PPG), polyethylene glycols (PEG), castor oil, polyols based on castor oil and other polyols based on oils of vegetable and animal origin, polyols based on polyester, polycaprolactones, polytetrahydrofurans, and hydroxy-functional polyacrylates. More preferably, the method of the invention is carried out using monoglycerides of fatty oils.

Preference is also given to the use of an isocyanate component in the method of the invention which includes one or more isocyanates selected from the group consisting of diisocyanatomethylbenzene (toluene diisocyanate (TDI)) and isomers and mixtures thereof, diisocyanatodiphenylmethane (diphenylmethane diisocyanate (MDI)) and isomers and homologs and mixtures thereof, 1,6-diisocyanatohexane (hexamethylene diisocyanate (HDI)), 3,5,5-trimethyl-1-isocyanato-3-isocyanatomethylcyclohexane (isophorone diisocyanate (IPDI)), 4,4'-diisocyanato-dicyclohexyl methane ($H_{12}$MDI) and isomers and mixtures thereof, 1,3-bis(isocyanato-methyl)benzene (m-xylylene diisocyanate (XDI)), 1,6-diisocyanato-2,2,4(2,2,4)-trimethylhexane (TMDI) and isomers and mixtures thereof, adducts of diisocyanates and polyhydric alcohols such as the adduct of diisocyanatomethylbenzene (TDI) with trimethylolpropane (TMP) available under the trade name DESMODUR L marketed by Bayer AG, oligomers of diisocyanates such as isocyanurates, biurets, allophanates, and uretdiones and prepolymers obtainable by the reaction of diisocyanates with hydroxy-functional polymers or oligomers. More preference is given to the use of diisocyanatodiphenylmethane (MDI) and isomers and homologs and mixtures thereof, adducts of diisocyanates and polyhydric alcohols such as the adduct of diisocyanato-methyl-benzene (TDI) with trimethylolpropane (TMP), oligomers of diisocyanates such as isocyanurates, biurets, allophanates and uretdiones, and prepolymers obtainable by the reaction of diisocyanates with hydroxy-functional polymers or oligomers, and most preference is given to the use of diisocyanatodiphenylmethane (MDI) and isomers and homologs and mixtures thereof.

Examples

Different anthraquinone dyes were used in the examples of the formulations A1 (filled) and A2 (unfilled) of the invention. The results are shown in Table 1.

| Formulation A1 | |
|---|---|
| Constituent | Percentage content by weight |
| Polyol component | |
| Castor oil | 5 to 50 |
| Polyol based on castor oil | 15 to 80 |
| Zeolite paste 50% strength | 1 to 10 |
| Talc | 10 to 70 |
| Rheology additive | 0.02 to 0.05 |
| Wetting agent | 0.02 to 0.5 |
| Antifoaming agent | 0 to 0.1 |
| Isocyanate component (curing agent) | |
| MDI | 50 to 100 |
| Catalyst | 0 to 10 |
| PPG 2000 | 0 to 50 |

| Formulation A2 | |
|---|---|
| Constituent | Percentage content by weight |
| Polyol component | |
| Castor oil | 5 to 50 |
| Castor oil-based polyol | 15 to 95 |
| Antifoaming agent | 0 to 0.1 |
| Isocyanate component (curing agent) | |
| MDI | 50 to 100 |
| Catalyst | 0 to 10 |
| PPG 2000 | 0 to 50 |

TABLE 1

| Dye | Concentration in ppm | Change of color |
|---|---|---|
| Formulation A1 | | |
| Solvent Blue 104 | 15 | blue to green |
| Solvent Green 3 | 15 | Petrol blue to green |
| Solvent Violet 59 | 15 | pink to red |
| Solvent Green 28 | 15 | bluish green to grass green |
| Solvent Violet 13 | 5 | violet to gray |
| Solvent Red 195 | 15 | dusky pink to pink |
| Formulation A2 | | |
| Solvent Blue 104 | 15 | blue to green |

The invention claimed is:

1. A curable composition comprising
at least one polyol component containing one or more polyols and
at least one isocyanate component containing one or more isocyanates,
wherein the at least one polyol component contains at least one color indicator in a concentration of from 0.1 to 500 ppm based on the weight of the polyol component and the color indicator has at least one quinonoid group; and
said color indicator is not a pH indicator.

2. The curable composition as defined in claim 1, wherein the at least one color indicator is an anthraquinone dye and/or an anthraquinone pigment.

3. The curable composition as defined in claim 1, wherein the at least one color indicator is selected from the group consisting of Solvent Blue 104, Solvent Green 3, Solvent Violet 59, Solvent Green 28, Solvent Violet 13, Solvent Red 195, Solvent Orange 60, Solvent Red 179, Disperse Violet 26, and Disperse Yellow 64.

4. The curable composition as defined in claim 1, wherein the isocyanate component contains further dyes and/or pigments.

5. The curable compositions as defined in claim 1, wherein the polyol component includes one or more polyols selected from the group consisting of polypropylene glycols, polyethylene glycols, polyols based on fats and/or oils, and polyols based on polyesters, polycaprolactones, polytetrahydrofurans and hydroxy-functional polyacrylates.

6. The curable compositions as defined in claim 5, wherein the polyol component includes polyols based on fats and/or oils, and wherein said polyols based on fats and/or oils are monoglycerides of fatty oils.

7. The curable composition as defined in claim 1, wherein the isocyanate component contains one or more isocyanates selected from the group consisting of diisocyanatomethylbenzene and isomers and mixtures thereof, diisocyanatodiphenylmethane and isomers and homologs and mixtures thereof, 1,6-diisocyanatohexane, 3,5,5-trimethyl-1-isocyanato-3-isocyanatomethylcyclohexane, 4,4'-diisocyanatodicyclohexylmethane and isomers and mixtures thereof, 1,3-bis(isocyanatomethyl)benzene, 1,6-diisocyanato-2,2,4-(2,2,4)-trimethylhexane and isomers and mixtures thereof, adducts of diisocyanates and polyhydric alcohols, oligomers of diisocyanates, and prepolymers obtainable by the reaction of diisocyanates with hydroxy-functional polymers or oligomers.

8. The curable composition as defined in claim 7, wherein the isocyanate component contains one or more isocyanates selected from the group consisting of diisocyanatodiphenylmethane and isomers, homologs, and mixtures thereof, adducts of diisocyanates and polyhydroxylic alcohols, oligomers of diisocyanates, and prepolymers obtainable by the reaction of diisocyanates with hydroxy-functional polymers or oligomers.

9. The curable composition as defined in claim 1, further comprising one or more further materials selected from the group consisting of fillers, catalysts, plasticizers, flame retardants, molecular sieves, and stabilizing agents.

10. A curable composition comprising
at least one polyol component containing one or more polyols and
at least one isocyanate component containing one or more isocyanates,
wherein the at least one polyol component contains at least one color indicator in a concentration of from 0.1 to 500 ppm based on the weight of the polyol component and the color indicator has at least one quinonoid group; and
said color indicator is not a pH indicator; and
wherein the polyol component includes one or more polyols selected from the group consisting of polypropylene glycols, polyethylene glycols, polyols based on fats and/or oils, and polyols based on polyesters, polycaprolactones, monoglycerides of fatty oils, polytetrahydrofurans, hydroxy-functional polyacrylates, castor oil, and a castor oil based polyol.

11. The curable composition as defined in claim 10,
wherein the polyol component is castor oil and a castor oil based polyol.

12. The curable composition as defined in claim 11,
wherein the polyol component is castor oil.

13. The curable composition as defined in claim 11,
wherein the polyol component is a castor oil based polyol.

14. The curable composition as defined in claim 10,
wherein the isocyanate component contains one or more isocyanates selected from the group consisting of diisocyanatomethylbenzene and isomers and mixtures thereof, diisocyanatodiphenylmethane and isomers and homologs and mixtures thereof, 1,6-diisocyanatohexane, 3,5,5-trimethyl-1-isocyanato-3-isocyanatomethylcyclohexane, 4,4'-diisocyanatodicyclohexylmethane and isomers and mixtures thereof, 1,3-bis(isocyanatomethyl)benzene, 1,6-diisocyanato-2,2,4-(2,2,4)-trimethylhexane and isomers and mixtures thereof, adducts of diisocyanates and polyhydric alcohols, oligomers of diisocyanates, and prepolymers obtainable by the reaction of diisocyanates with hydroxy-functional polymers or oligomers.

15. The curable composition as defined in claim 14,
wherein the isocyanate component contains one or more isocyanates selected from the group consisting of diisocyanatodiphenylmethane and isomers, homologs, and mixtures thereof, adducts of diisocyanates and polyhydroxylic alcohols, oligomers of diisocyanates, and prepolymers obtainable by the reaction of diisocyanates with hydroxy-functional polymers or oligomers.

16. A curable composition comprising
at least one polyol component containing one or more polyols and
at least one isocyanate component containing one or more isocyanates,
wherein the at least one polyol component contains at least one color indicator in a concentration of from 0.1 to 500 ppm based on the weight of the polyol component and the color indicator has at least one quinonoid group; and
wherein the polyol component consists essentially of:
castor oil in the concentration of 5 to 50 percent content by weight, polyol based on castor oil in the concentration of 15 to 80 percent content by weight, zeolite paste 50% strength in the concentration of 1 to 10 percent content by weight, talc in the concentration of 10 to 70 percent content by weight, rheology additive in the concentration of 0.02 to 0.05 percent content by weight, wetting agent in the concentration of 0.02 to 0.05 percent content by weight, antifoaming agent in the concentration of 0 to 0.1 percent content by weight,
and wherein the percentage by weight of each constituent is based on the weight of the polyol component.

17. The curable composition as defined in claim 16,
wherein the isocyanate component consists essentially of:
diisocyanatodiphenylmethane in the concentration of 50 to 100 percent content by weight, catalyst in the concentration of 0 to 10 percent content by weight, polypropylene glycol in the concentration of 0 to 50 percent content by weight,
and wherein the percentage by weight of each constituent is based on the weight of the isocyanate component.

18. A curable composition comprising
at least one polyol component containing one or more polyols and
at least one isocyanate component containing one or more isocyanates,
wherein the at least one polyol component contains at least one color indicator in a concentration of from 0.1 to 500 ppm based on the weight of the polyol component and the color indicator has at least one quinonoid group; and
wherein the polyol component consists essentially of:
caster oil in the concentration of 5 to 50 percent content by weight, caster oil based polyol in the concentration of 15 to 95 percent content by weight, antifoaming agent in the concentration of 0 to 0.1 percent content by weight,
and wherein the percentage by weight of each constituent is based on the weight of the polyol component.

19. The curable composition as defined in claim 18,
wherein the isocyanate component consists essentially of:
diisocyanatodiphenylmethane in the concentration of 50 to 100 percent content by weight, catalyst in the concentration of 0 to 10 percent content by weight, polypropylene glycol in the concentration of 0 to 50 percent content by weight,
and wherein the percentage by weight of each constituent is based upon the weight of the isocyanate component.

* * * * *